(12) United States Patent
Midha et al.

(10) Patent No.: US 6,312,716 B1
(45) Date of Patent: *Nov. 6, 2001

(54) PATCH AND METHOD FOR TRANSDERMAL DELIVERY OF BUPROPION BASE

(75) Inventors: Kamal K. Midha, Hamilton (BM); Hans E. Junginger; Mark Hirsh, both of Wellesley, MA (US)

(73) Assignee: Peierce Management LLC, Wellesley, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/562,178

(22) Filed: May 2, 2000

Related U.S. Application Data (63) Continuation-in-part of application No. 09/309,075, filed on May 10, 1999.

(51) Int. Cl.[7] .................................................. A61F 13/02
(52) U.S. Cl. ........................... 424/448; 514/649; 514/769; 514/772
(58) Field of Search .............................. 424/448; 514/649, 514/769, 772

(56) References Cited

FOREIGN PATENT DOCUMENTS

| 9938502 | * | 8/1999 | (WO) . |
| 9938503 | * | 8/1999 | (WO) . |

* cited by examiner

*Primary Examiner*—Michael A. Williamson
(74) *Attorney, Agent, or Firm*—Herbert Dubno; Jonathan Myers (57) ABSTRACT

The invention includes a patch and method for transdermal delivery of bupropion base. In the method of this invention, a patient is administered a bupropion base in an amount effective to alleviate withdrawal symptoms and to prevent or reduce craving of nicotine in said patient. Alternatively, an effective amount of bupropion base is delivered to alleviate depression in a patient or to treat obesity. A transdermal patch includes a bupropion base. The bupropion base can be mixed with an acceptable pharmaceutical carrier.

14 Claims, 5 Drawing Sheets

PATCH AND METHOD FOR TRANSDERMAL DELIVERY OF BUPROPION BASE

CROSS REFERENCE TO RELATED APPLICATIONS

This application is a continuation-in-part of copending U.S. patent application Ser. No. 09/309,075 filed May 10, 1999, the entire teachings of which are incorporated herein by reference.

FIELD OF THE INVENTION

This application relates to a method of transdermally administering bupropion base to a mammal to treat depression and to alleviate withdrawal symptoms from tobacco smoking thereby enhancing the ability of a patient to abstain from smoking. More particularly the invention relates to a patch containing stabilized bupropion base enabling successful transdermal administration of bupropion base to a patient.

BACKGROUND OF THE INVENTION

Bupropion hydrochloride is a known antidepressant sold in immediate release and sustained release tablet form under the brand names WELLBUTRIN® and ZYBAN®. Bupropion hydrochloride is an antidepressant of the aminoketone class and is chemically unrelated to tricyclic, tetracyclic, selective serotonin re-uptake inhibitors or other known antidepressant agents. Bupropion (BUP) hydrochloride is highly metabolized in both rats and humans. The major metabolites are the erythroamino alcohol (EB), the threoamino alcohol (TB), and the hydroxy metabolite (HB). The metabolites exhibit pharmacological activity in an antitetrabenzene model. Bupropion hydrochloride is also used in preventing functional impairment and drowsiness seen upon administration of benzodiazepine, in the treatment of minimal brain dysfunction, tardive dyskinesia, impaired mental alertness upon ingestion of ethanol and psychosexual dysfunction and in promoting weight loss. While the immediate release and sustained release tablets currently sold are suitable for the indicated use, there is a disadvantage to bupropion hydrochloride in that there can be an accumulation of metabolites that can be detrimental to one's health.

In a study of pharmacokinetics of bupropion hydrochloride in the elderly, six elderly patients with diagnosed depression were examined in a single and multiple dose study. Half-lives (t1/2app) of the metabolites TB, EB and HB were 38.8+/−7.6 hours, 61.4 +/−21.6 hours and 34.2 +/−4.6 hours, respectively. After multiple dosing, the half-life for bupropion and its metabolites did not change significantly although in some patients the half-life of metabolites was substantially prolonged. In addition, there was also evidence of inordinate accumulation of metabolites. The elderly are at risk for accumulation of bupropion and its metabolites. See *J. Clin. Pharmacol.* 35:876–884 (1995).

Therefore a need exists for a new form of bupropion for delivery to the body while minimizing the formation of metabolites.

According to WO 99/11208 to Williams et al, an attempt was made to prepare bupropion hydrochloride in the form of a composition to be administered transdermally. According to Examples 5 and 19 of this patent publication, a transdermal system was prepared by grinding tablets of bupropion hydrochloride to a fine powder which was dissolved in purified water, filtered and used to make a 20% pluronic gel. This gel and soya lecithin were mixed with syringes and diluted further with pluronic gel F127 to obtain a total of two 60 c.c. batches of bupropion hydrochloride having a strength of 15 mg/ml.

Furthermore, this gel was applied by each of the 3 patients (self-administered) to the skin for a period of 1 hour. The dosage of 50 to 200 mg/day was made in one example.

The administered gel did not deliver the drug bupropion (or at least enough bupropion) into the systemic circulation as no clinical responses or measurable levels of bupropion were noted after its application to the skin for a period of at least one hour according to Example 31. Williams et al express the conclusion on page 19 that both the laboratory measure and the patient clinical response indicated poor or equivocal absorption and results for transdermally administered bupropion hydrochloride.

According to Williams et al bupropion tablets were ground to dissolve the bupropion in water, filtered and then used in gel formulation. Bupropion tablets marketed worldwide contain (+/−) bupropion hydrochloride which is highly water-soluble. Bupropion hydrochloride is the HCl salt of an aminoketone which is not very stable; therefore it needs to be stabilized in tablet formations. Moreover, as a hydrochloride salt, bupropion HCl cannot be easily transported through the skin. The absorption of bupropion HCl into the systemic circulation requires that the hydrochloride salt be converted to base bupropion which is much more unstable. Even if in the gel matrix made from Pluronic F127 NF and potassium sorbate, bupropion hydrochloride is converted into bupropion base, the question arises as to how this base was stabilized. Bupropion base needs to be stabilized; otherwise the base undergoes decomposition.

U.S. Pat. No. 5,358,970 to Ruff et al discloses bupropion hydrochloride stabilized with a number of acidic stabilizing agents including L-cysteine hydrochloride, glycine hydrochloride, malic acid, sodium metabisulfite, citric acid, tartaric acid, and L-cysteine dihydrochloride. The stabilized bupropion hydrochloride is in the form of a solid pharmaceutical composition that may be employed in tablets or capsules. There is no disclosure or suggestion of stabilizing bupropion base nor is there a disclosure or suggestion of preparing a composition containing any form of bupropion in a composition suitable for transdermal administration.

WO 99/38503 to McCullough et al and WO 99/38502 and 99/38504 to Young each disclose an optically active form of bupropion or bupropion in the form of a pharmaceutically acceptable salt in the treatment of depression or to facilitate the stopping of smoking tobacco. Many methods of administration are disclosed including transdermal administration although there is no example or any further information as to how a composition suitable for transdermal administrations could be prepared. Reference is made to U.S. Pat. No. 5,358,970 to Ruff et al and to the stabilizers disclosed therein. It is stated in each of WO 99/38503, WO 99/38502 and WO99/38504 that these stabilizers may be used to stabilize the bupropion or the bupropion salts. All three of these patent publications exemplify these stabilizers only in combination with bupropion hydrochloride in a form suitable for oral administration.

Bupropion hydrochloride and other bupropion acid addition salts do not cross the dermal barrier by passive diffusion and require a different active mechanism. For facile delivery across the skin into the systemic circulation it is generally required that the bupropion acid addition salts be converted into the base form of the drug and therefore require bases to neutralize the acid. These manipulations would cause complications and could adversely affect the continuous, uninterrupted, and optimal delivery of bupropion from a transdermal system into the systemic circulation.

OBJECTS OF THE INVENTION

It is an object of the invention to provide a method of transdermally administering bupropion base to a patient to treat depression, promote weight loss, and alleviate withdrawal symptoms from tobacco smoking thereby enhancing the ability of a patient to abstain from smoking as well as to treat attention deficit disorder (ADD) and attention deficit hyperactivity disorder (ADHD).

It is a further object of the invention to provide a patch containing stabilized bupropion base enabling successful transdermal administration of bupropion base to a patient.

It is a further object of the invention to provide transdermal administration of bupropion free base to a patient while minimizing in vivo formation of bupropion metabolites thereby reducing the dose required for such a patient. The other object of the invention is to provide via a transdermal route delivery of optimal and almost steady levels (with no peaks and troughs) of burpropion thereby reducing the risk of seizures associated with bupropion given as immediate release.

SUMMARY OF THE INVENTION

The invention includes a patch containing bupropion base as well as a method of transdermally administering the bupropion base to a patient in need of bupropion.

According to the method of treating a patient (human subject) the following steps are carried out:

stabilizing a bupropion base selected from the group which consists of (+)-bupropion base, (−)-bupropion base and racemic bupropion base and mixtures thereof by combining the bupropion base with at least one stabilizer capable of stabilizing the bupropion base in the absence of any additional base and forming a composition capable of transferring predominantly across the stratum corneum which is recognized to be the main barrier of the skin for delivery of therapeutic compounds;

incorporating the stabilized bupropion base on a support in a transdermal patch having a bupropion-transfer surface area adapted to contact the skin of the patient and sufficient to transfer a therapeutically effective amount of bupropion base through the skin of said patient into the bloodstream of said patient, said patch containing bupropion base as the sole base; and adhering said patch to the skin of the patient for a period of days to deliver a bupropion dosage of substantially 10 mg/day to 300 mg/day to said patient.

According to one feature of the invention, the stabilizer is a pharmaceutically acceptable organic acid ester. Examples of such stabilizers include 1-ascorbic acid palmitate, and L-ascorbic acid G palpitate. Preferably the stabilizer comprises 2.7 to 27% by weight of the bupropion base in the composition, more preferably 3 to 15% by weight of the bupropion base, and most preferably 5 to 8% by weight of the bupropion base.

According to another feature of the invention the stabilizer is Vitamin E or butylated hydroxy anisole. The preferred forms of Vitamin E include tocopherol solution in alcohol, Vitamin E succinate, and Vitamin E 700 acetate. Once again the amount of the stabilizer employed comprises 2.7 to 27% by weight of the bupropion base in the composition, more preferably 3 to 15% by weight of the bupropion base, and most preferably 5 to 8% by weight of the bupropion base.

We have found that the Vitamin E and the butylated hydroxy anisole are especially good stabilizing agents for the bupropion base. The fact that these particular stabilizing agents are antioxidants and are not acidic may contribute to the highly successful stabilization of the bupropion base.

The invention further comprises a patch for transdermal delivery of bupropion base to a patient, said patch comprising:

(a) a flexible, inert backing layer incapable of absorbing bupropion base;

(b) a release liner through which bupropion base is not permeable; and (c) a reservoir located between the backing layer and the release liner, said reservoir having a bupropion-transfer surface adjacent to the release liner and adapted to contact the skin of the patient and sufficient to transfer an effective dosage of bupropion base through the skin of said patient into the bloodstream of said patient, said reservoir containing bupropion base as the sole base, which comprises:

(i) a therapeutically effective amount of bupropion base selected from the group which consists of (+)-bupropion base, (−)-bupropion base and racemic bupropion base and mixtures thereof on said support;

(ii) at least one stabilizer capable of stabilizing the bupropion base in said reservoir, said stabilizer selected from the group consisting of Vitamin E and butylated hydroxy anisole; and (iii) means for securing the bupropion-transfer surface area of said reservoir to the skin of the patient.

The preferred form of Vitamin E includes tocopherol solution in alcohol, Vitamin E succinate, and Vitamin E 700 acetate. Once again the amount of the stabilizer employed comprises 2.7 to 27% by weight of the bupropion base in the composition, more preferably 3 to 15% by weight of the bupropion base, and most preferably 5 to 8% by weight of the bupropion base.

The present invention is directed to a patch containing bupropion base and method for transdermal delivery of bupropion base. A method includes administering medicament to a mammalian body, including the central nervous system, wherein a therapeutically effective amount of said medicament is transdermally administered to a mammal, preferably a human. The term "transdermal delivery" includes both transdermal (or "percutaneous" and transmucosal administration, which is delivery by passage of a drug through the skin or mucosal tissue and into the bloodstream. The term "therapeutically effective" amount means a sufficient amount of a compound to provide the desired therapeutic effect that is effective in relieving symptoms of the condition or disease being treated with minimal side effects. An "effective" amount of a permeation enhancer composition means an amount that provides a desired increase in skin permeability and, correspondingly, the desired depth of penetration, rate of administration, and amount of drug delivered.

An improvement of the present invention includes selecting a route of delivery to avoid increased formation of an unwanted and/or adverse metabolites), such as those produced by the gastrointestinal tract and liver when the medicaments are administered orally. In the present invention, the medicament is placed in a suitable transdermal patch formulation for dermally administering a therapeutically effective amount of the medicament to bypass the gastrointestinal tract absorption and first pass metabolism in the liver and thereby to decrease the formation of the unwanted metabolites in the human body including the central nervous system. This transdermal patch is utilized over a period of one or more days to achieve sustained high levels of the medicament.

The amount of therapeutic dose can be reduced via transdermal delivery. Therapeutic dosages can be reduced thereby reducing adverse effects. The most serious adverse effects is the increased incidence of seizures. In addition, other frequently reported adverse effects associated with the use of bupropion includes nausea, vomiting, excitement, agitation, blurred vision, restlessness, postural tremor, and some hallucinations/confusional states with the potential for abuse. Other adverse or side effects associated with bupropion includes but are not limited to anxiety, insomnia, headaches, and/or migraines, dry mouth, constipation, tremor, sleeping disturbances, dermatological problems (e.g. rashes), neuropsychiatric signs and symptoms See, the Physician's Desk Reference® (2000). These effects are dose limiting in a number of patients. In Parkinsonian patients, the adverse effects can be the particular toxicity of bupropion or the results of a drug interaction (as most patients were receiving concomitant levodopa). The transdermal system of delivering bupropion allows dosing of one time/day or potentially one time over a period of three days.

The bupropion base can be stabilized with other substances for example, 1-ascorbic acid palmitate, the range of these ingredients can be from about 2.7% to about 27%. The composition of the bupropion base is in liquid or semi solid form. The transdermal patch system delivers active bupropion and therefore can provide therapeutic levels which are devoid of peaks and troughs causing fewer or no side effects. Because the bupropion base does not enter the gastrointestinal system and forms substantially no metabolites, the precaution attending to reduced liver function may be reduced or eliminated. This reduction in metabolism (catabolism) due to transdermal delivery results in lower doses of the drug being required for therapeutic efficacy with reduced side effects. The transdermal delivery system allows steady state delivery, reduces large fluctuation of bupropion in the blood, and allows the optimal steady levels to be achieved quicker.

For smoking cessation, treating depression and obesity, the transdermal system offers a more effective delivery system as the patient does not have to remember to take the oral tablets as specified times. Patients who have reduced hepatic functions or other liver disease because of chronic intake of alcohol are at a reduced risk from using bupropion in the delivery system. Individuals who have a reduced renal function are not prevented from using bupropion because there are negligible amounts of metabolites produced. The incidence of seizures can be reduced because seizures are dose dependent and it can be anticipated that a lower does of bupropion is necessary as the transdermal system allows the bupropion to enter the blood without passing through the gastrointestinal system and liver.

Also contemplated within the scope of the invention is the treatment of Parkinson's disease in a patient while avoiding the concomitant liability of adverse effects associated with the administration of bupropion through the use of a transdermal system where bupropion base includes a racemic mixture of bupropion isomers.

The invention further includes a method of treating bipolar disorders, attention deficit disorders, conduct disorders, psycho-sexual dysfunction, bulimia, eating disorders and specific food cravings by the transdermal administration at a therapeutically effective amount of bupropion base either as the racemate or in the form of one of its optical isomers.

In one embodiment, the transdermal system contains bupropion base either as the racemate or as the (+) isomer or as the (−) isomer in acrylic-based polymer pressure sensitive adhesives with a resinous cross-linking agent (either based on silicone polymers or polyacrylates and alcohol) to provide a continuous source of active ingredients. Each unit is sealed in a paper polyethylene-foil pouch. Isomers of bupropion can be separated by known methods. Stabilizers in the reservoir of the patch include Vitamin E preferably as DL Tocopheral solution in alcohol, Vitamin E succinate or Vitamin E 700 acetate and butylated hydroxy anisole. Examples of suitable transdermal delivery systems for bupropion base include systems disclosed in U.S. Pat. Nos. 5,834,011, 5,840,327 and 5,879,701. The teachings of each patent are incorporated by reference herein.

The reservoir may include a carrier or vehicle. The "Carriers" or "vehicles" refer to carrier materials suitable for transdermal drug administration and include any such materials known in the art, such as any liquid, gel solvent, liquid diluent, solubilizer, or the like, which is nontoxic and which does not interact with other components of the composition in a deleterious manner. Examples of suitable carriers for use herein include water, silicone, liquid sugars, waxes, petroleum jelly, and a variety of other materials. The term "carrier" or "vehicle" can also refer to crystallization inhibitors, or other types of additives useful for facilitating transdermal drug delivery. Suitable materials for this layer include, for example, polysiloxanes, polyisobutylenes, polyurethanes, plasticized ethylenevinyl acetate copolymers, low molecular weight polyether amide block polymers (e.g., PEBAX), tacky rubbers, such as polyisobutene, polystyrene-isoprene copolymers, polystyrene-butadiene copolymers, and mixtures thereof. Presently preferred adhesive materials for use as reservoir layer are polyisobutylenes, silicones, polyurethanes and polyacrylates, with polyisobutylenes particularly preferred. The carrier will be composed of these materials in such a way to achieve a controlled occlusion of the skin achieving optimal enhancement of drug penetration across the skin with minimal skin irritation (which may be caused by complete occlusivity of the system).

In a preferred embodiment, the reservoir matrix may include a dispersing agent which aids in maintaining the particulate phase dispersed in the continuous phase. In other embodiments, non-ionic excipients, such as lauric alcohol, propylene glycol monolaurate, myristyl lactate, lauryl lactate, or the like, facilitate dispersion.

The cold flow properties of the polymer adhesives of the bupropion delivery system are considered acceptable when adhesion of the transdermal patch to the skin of the user remains high throughout the drug delivery period and the adhesive does not extend beyond the boundary of the patch.

The release liner is a disposable element which protects the device prior to application. Typically, the release liner is formed form a material impermeable to the drug, vehicle and adhesive, and which is easily stripped from the contact adhesive. Release liners are typically treated with silicone or fluorocarbons. Silicone-coated polyester is a preferred embodiment. Another material may be silicone-coated aluminum.

The backing layer functions as the primary structural element of the device and provides the device with much of its flexibility, drape and, preferably, controlled occlusivity. The material used for the backing layer should be inert and incapable of absorbing drug, enhancer or other components of the pharmaceutical composition contained within the device. The backing is preferably made of one or more sheets or films of a flexible material that serves as a protective covering to prevent loss of drug or vehicle or both by transmission through the upper surface of the device, and imparts a desired degree of occlusivity to the device, such that the area of the skin covered on application becomes hydrated. The material used for the backing layer may permit the device to follow the contours of the skin and be worn comfortably on areas of the skin, such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 15 micrometers to about 20 micrometers in thickness.

The bupropion transdermal infusion system is a flat unit designed to provide continuous controlled release of bupropion base as racemate or its isomers through the intact skin. The rate of release of bupropion base or its isomers is linearly dependent upon the area of the applied system; each square cm of the applied system delivers approximately 2 mg to 7.5 mg/cm$^2$. In one embodiment, the patch size can range from about five to forty square centimeters. The rate of delivery of the bupropion from a forty square centimeter patch can range from about 10 mg/day to 300 mg/day for all methods of treatment.

Bupropion hydrochloride is commercially available under the name Wellbutrin and Wellbutrin from Burroughs Wellcome. For bupropion (1-(3-chlorophenyl-Z-[(1,1-dimethylethyl)amino]-1-propanone, its preparation is described in U.S. Pat. Nos. 3,819,706 and 3,885,046, wherein the teachings of each patent are incorporated by reference.

Preparation of bupropion base can be carried out by a suitable method. In one embodiment, 1.2 g bupropion HCl is dissolved in 20 ml of distilled water to which 0.1 N NaOH is added until the pH is about 12. Then this mixture is extracted with 50 ml of diethylether by shaking followed by centrifugation. The ether phase containing the bupropion base is separated and the remaining watery phase is treated three times with 80 ml diethylether. The unified ether phases are dried (removal of residual water) by adding 15 g anhydrous $K_2CO_3$, filtrated and the ether is evaporated at 50° C. under vacuum (rotavapor). The residual phase (bupropion base) (1.0 g) is dissolved in 6 ml propylene glycol and stored until further use under nitrogen gas in a tight bottle in the dark. Bupropion base can be prepared by other procedures that are known as state of the art.

In humans, bupropion metabolism occurs via the reduction of its carbonyl group and/or the hydroxylation of its tertiary butyl group. According to the U.S. Food and Drug Administrations's Summary Basis of Approval (SBA), nine metabolites have been identified in urine, four of which have shown activity in mice. These are erythro amino alcohol, threo amino alcohol, erythro amino diol, and morpholindolmetabolite, which is formed from the hydroxylation of the t-butyl group.

Bupropion undergoes a vary rapid first pass metabolism. Absolute bioavailability is generally not determinable in humans because of the lack of availability of an intravenous dosage form. In rats and dogs, the absolute bioavailability is in the range of about five to twenty percent. $C_{max}$ is the maximum concentration of the drug in plasma and blood.

Following oral dosage, drug blood or plasma concentration is dose proportional from 100 to 250 mgs $C_{max}$ occurs in approximately 2 hours, and its biological half life is approximately 14 hours (range 8–24 hours). Following oral administration of radio-labeled carbon 14 bupropion, 87% of the radioactivity is recovered in the urine and 10% in the feces. As expected from the extensive first pass metabolism, less than 0.5% is excreted as unchanged drug. Bupropion is 80% bound to albumin and its (single) oral dose kinetics is best described by a 2 compartment open model with first order absorption.

The morpholino metabolite (MM) is half as potent (antidepressive effect) as parent medicament and appears in the systemic circulation almost as fast, following the administration of a single oral dose. The MM $C_{max}$ is three times and its AUC is fifteen times, that of parent medicament drug. Its biological half-life $t_{1/2}$=24 hours. The threo amino alcohol metabolite (TAM) is also half as potent as a medicament (antidepressive effect), and its kinetics parallel that of MM. The erythro amino alcohol and erythro amino diol metabolites are generally not quantifiable after a 100 mg, single, oral dose.

According to the SBA, studies in mouse, rat, and dog, show that bupropion induces its own metabolism. The mouse shows a 58% reduction over ten days, and the dog, 76 and 90% reductions at two different dose levels over one year of treatment. Metabolites have half-lives exceeding that of parent drugs, with resultant significant metabolite accumulation after administration of multiple doses.

EXAMPLE 1

Preparation of a stabilized bupropion base transdermal patch.

The following composition is contained in the reservoir:

| Component | % w/w on a dry basis |
|---|---|
| 1. racemic bupropion base | 18 |
| 2. polyisobutylene adhesive | 20 |
| 3. Vitamin E succinate | 2 |
| 4 petroleum jelly | 60 |

Racemic bupropion base (18 g), Vitamin E succinate (2 g), polyisobutylene adhesive (20 g) and petroleum jelly (60 g) are mixed at ambient temperature until all of the ingredients have dissolved. The mixture is allowed to stand for several minutes to remove air bubbles.

The mixture was formulated into a patch system as follows:

Using an appropriate coating device (square tool steel Multi-Clearance Applicator sold by BYC Gardner) with a 5 or 10 mil (about 130 to 250 microns) casting gap, a layer of the mixture was coated onto a polyester backing layer having a thickness of about 100 microns, and dried in an oven at 76 to 78° C. for 15 to 18 minutes. A silicone-coated polyester release liner was then laminated onto the opposite side of the mixture of the backing layer.

The multi-layer system was then cut into a 5 cm square patch. The thickness of the patch is about 500 microns.

EXAMPLE 2

The same procedures and conditions were applied as in Example 1 except that the racemic bupropion base was replaced by (+)-bupropion base.

EXAMPLE 3

The same procedures and conditions were applied as in Example 1 except that the racemic bupropion base was replaced by (−)-bupropion base.

EXAMPLE 4

The same procedures and conditions were applied as in Example 1 except that the Vitamin E succinate was replaced in whole or in part by butylated hydroxy anisole.

DETAILED DESCRIPTION OF THE DRAWINGS

Figure 1:
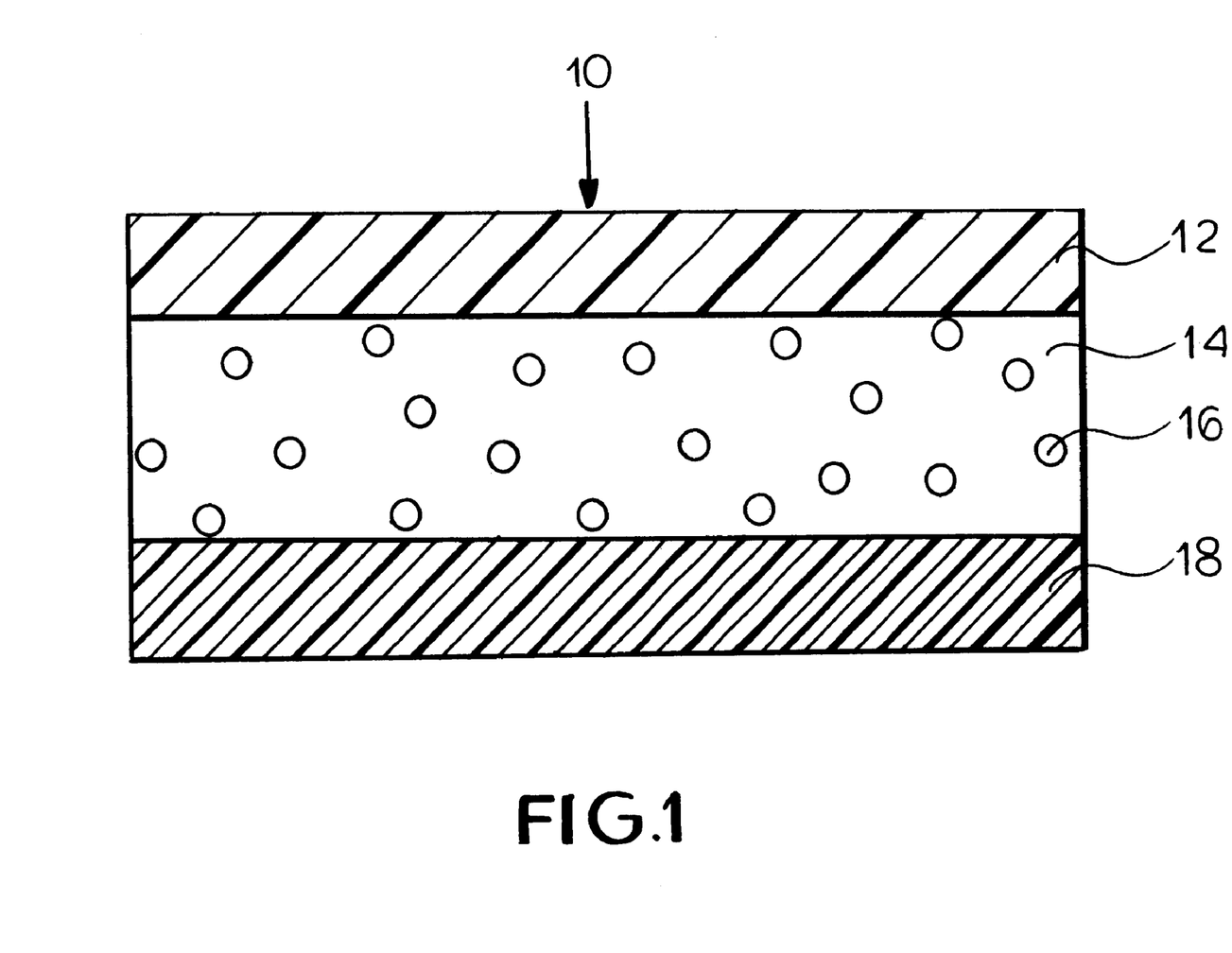
FIG. 1 is a schematic illustration of a transdermal delivery system (patch) for use according to the present invention.

Reservoir layer 14 in FIG. 1 is a means for containing the drug and an adhesive for securing the patch to the skin during use. As release liner 18 is removed prior to the application of the patch to the skin, reservoir layer 14 serves as the basal surface of the patch which adheres to the skin. Reservoir layer 14 includes a pressure-sensitive adhesive suitable for long term skin contact. Reservoir layer 14 is physically and chemically compatible with bupropion and the carriers and vehicles employed.

BIOLOGICAL EXAMPLES

Flux Studies Using Full Thickness Human Skin

Preparation of Human Stratum Corneum Samples

Human abdominal skin obtained by surgical operation was processed immediately upon arrival on the day of surgery. After the removal of subcutaneous fat, the skin was dermatomed using an electric dermatome (Padgette Dermatome, Kansas City, USA) to a thickness of approximately 250 $\mu$m. The sheets were used the same days as obtained for diffusion experiments. Until use, the sheets were kept dermal side down in a Petri humidity disk.

Formulation of the Donor Solutions

For standardization, saturated solutions of bupropion in propylene glycol were made and 80% of the saturated solution was used as donor solutions. 1.1 g bupropion has been suspended in 6.0 ml propylene glycol and was vortexed at 90 rpm for 68 hours at 32° C. in a thermostated shaking cupboard. Controls have been done every 24 hours to assure that sufficient undissolved drug was in the vessel. Thereafter the suspension was centrifuged (3,000 rpm) for 10 minutes and the clear supernatant was used as saturated solution.

For the diffusion experiments the donor solutions were freshly prepared for each experiment, 550 mg of the bupropion base were suspended in 3.0 ml propylene glycol (PG) and treated as previously described. To the saturated supernatant, PG was added to result in a 80% saturated solution, from which the drug content was analyzed (104 mg/ml PG).

Formulation of the Acceptor Solution

Phosphate buffered saline (PBS) was used as acceptor solution and was freshly made and degassed with a vacuum pump before each experiment. PBS buffer solution pH 7.4 had the following composition: NaCl, 8 g/l; $Na_2HPO_4 2H_2O$, 1.4 g/l; KCl, 0.2 g/l, $KH_2PO_4$, 0.2 g/l; $NaN_3$, 1.0 g/l and 5 ml Streptomycin/penicillin solution (5,000 units in 0.9% NaCl).

Transdermal Permeation Studies

Figure 2:
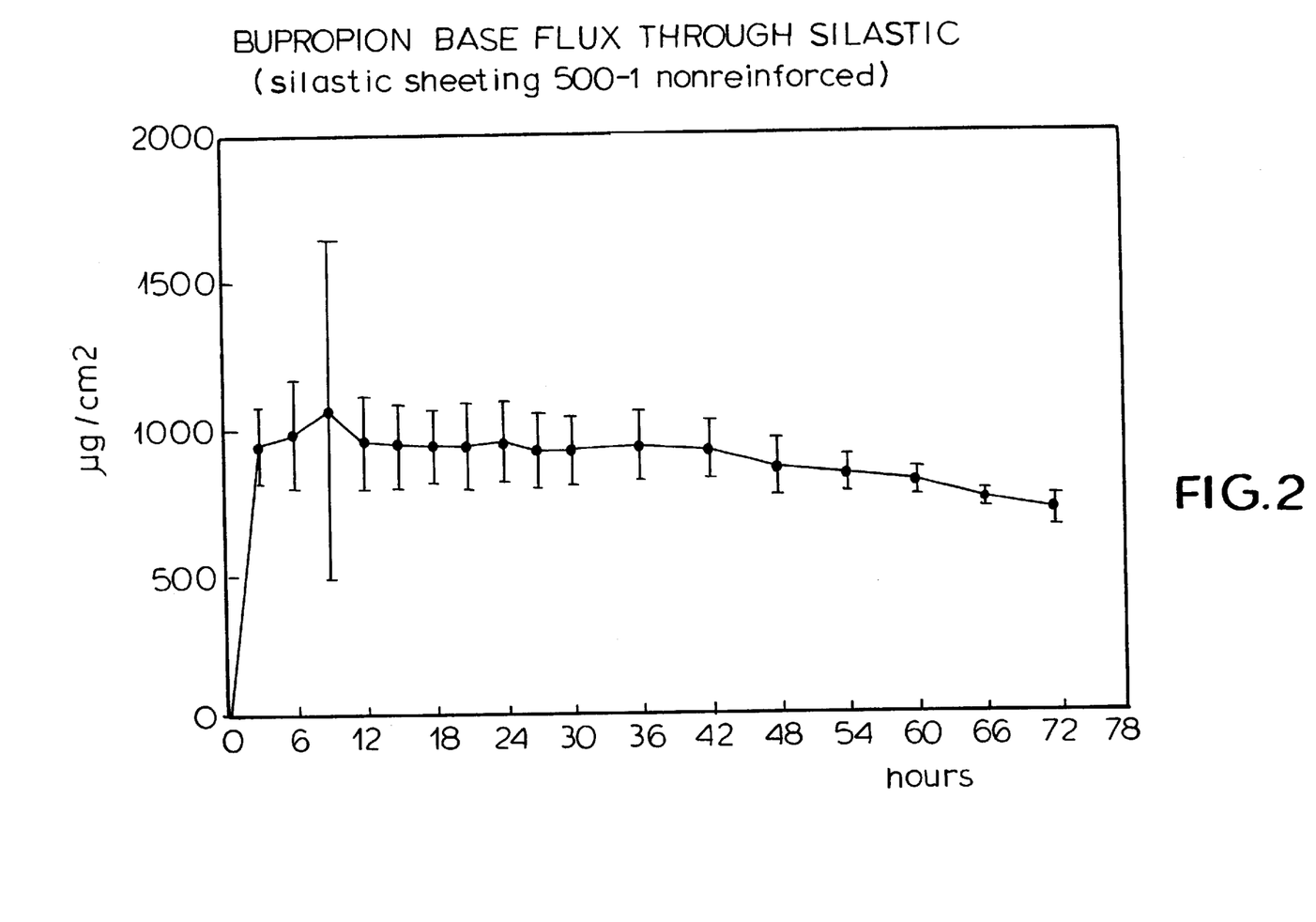
FIG. 2 is a graph plotting time against the amount of bupropion base flux through silastic sheeting in a patch.
Figure 3:
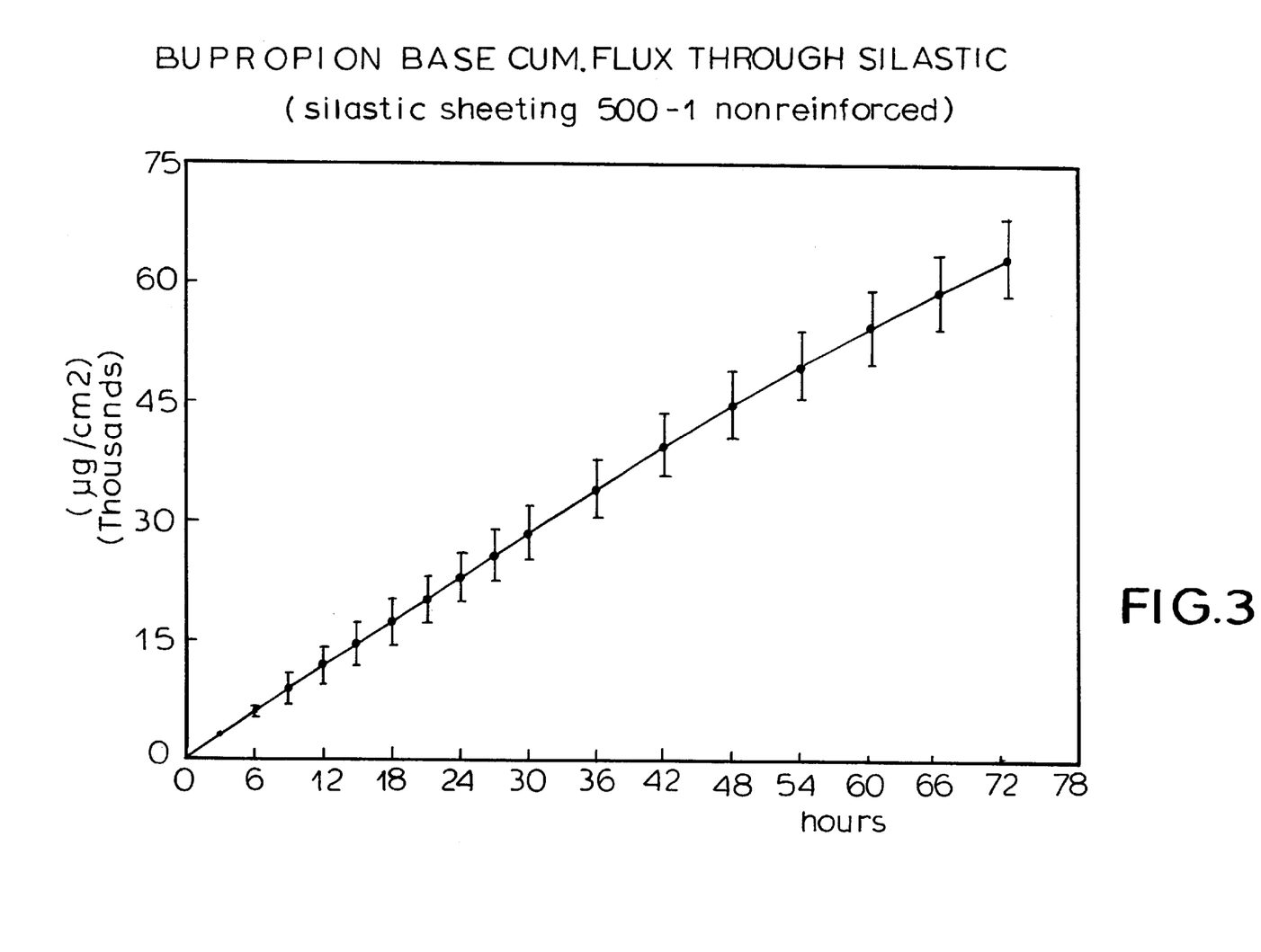
FIG. 3 is a graph plotting time against the amount of bupropion base cumulative flux through silastic sheeting in a patch.
Figure 4:
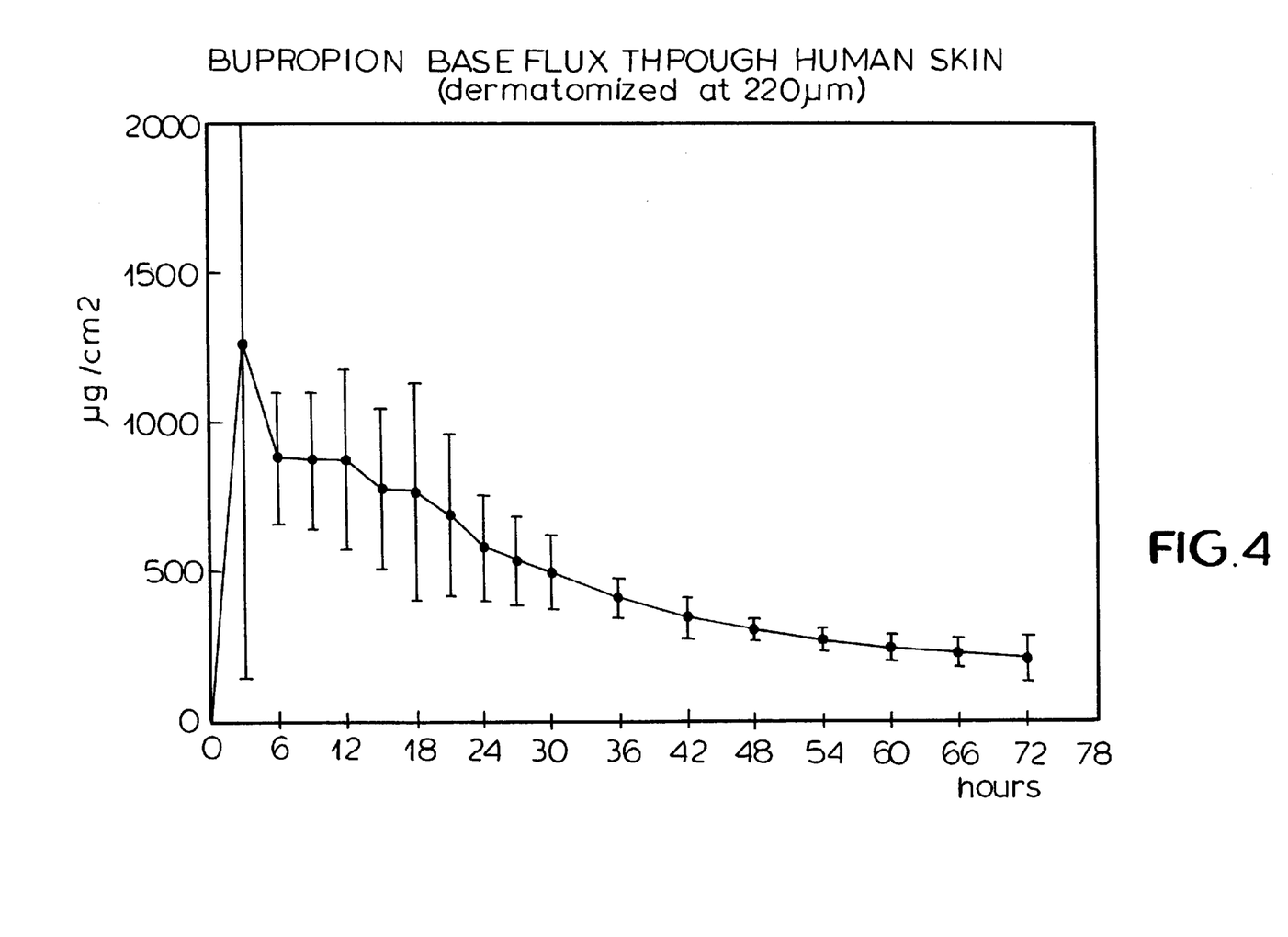
FIG. 4 is a graph plotting time against the amount of bupropion base flux through human skin dermatomized at 250 micrometers in an in vitro test.
Figure 5:
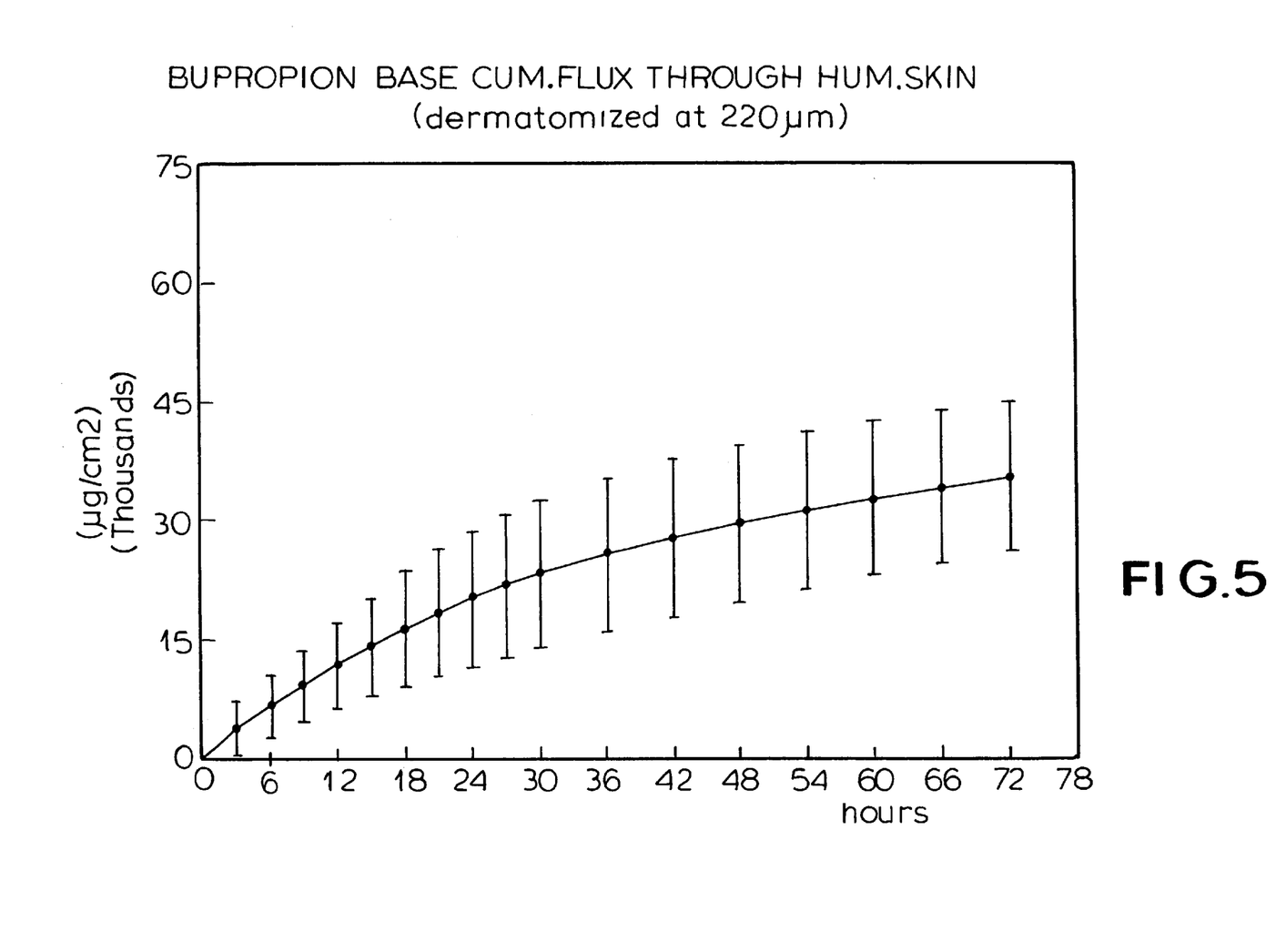
FIG. 5 is a graph plotting time against the amount of bupropion base cumulative flux through human skin dermatomized at 220 micrometers in an in vitro test.

Transdermal permeation studies with bupropion across human stratum corneum or dermatomized skin were performed as follows: The diffusion cells used have been described by Tanojo et al (J. Control. Rel. 45 (1997) 41–47). The original donor part of the described cell design has been modified in such a way that the spiral has been replaced by a donor chamber of 700 $\mu$l volume. To assure complete contact of the skin membrane adduct with the spiral of the acceptor phase, a slight pressure of the donor phase to the membrane adduct was achieved by closing the donor chamber with a moveable disk connected with a spring to exert the pressure. Pieces of 18 mm diameter of dermatomized skin have been punched and used. To prevent the dermatomized skin from further hydration in the diffusion experiments with bupropion the sheets were sandwiched between two silastic sheetings (500-1, non-reinforced, Dow Corning USA) with the both sides fixed with medical adhesive (Dow Corning USA). FIG. 2 shows the results of flux by bupropion base across silastic sheeting. FIG. 3 shows the results of the cumulative flux by bupropion base across silastic sheeting. The sandwiched dermatomized skin sheets have been mounted between the two parts of the diffusion cell. The diffusion area was 55.2 square millimeters. The acceptor phase was pumped through the spiral of the acceptor chamber with a rate of 5 ml/hr (Ismatec, Dijkstra, Lelystad, The Netherlands). During the experiments, the diffusion cells were placed in a water bath thermostated at 32° C. Samples were taken every 3 hours until the end of the experiments (72 hours) and sampled by a fraction collector (Retriever III, Beun de Rone, Abcoude, The Netherlands). FIG. 4 shows the results of flux by bupropion base through human skin dermatomized at 220 micrometers. FIG. 5 shows the results of cumulative flux by bupropion base through human skin dermatomized at 220 micrometers.

HPLC Analysis

A spectroflow 400 pump (Separations, Hendrik Ido Ambacht, The Netherlands) was used to deliver the mobile phase, consisting of acetonitrile 0.1 m $KH_2PO_4$ pH3 20:80 (v/v) with a flow rate of 0.8 ml/min. The mobile phase was degassed with a vacuum pump and chromatography was performed at ambient temperature. Sample amounts of 20 $\mu$m were injected with a Gilson model 321 autosampler (Gilson Middleton, Wis. USA) with a 20 microliter loop built in onto a inertsil 5 ODS column (Chrompack Nederland BV, Bergen Op Zoom, The Netherlands). This analytical column was proceeded by a chromspher 5C18 guard column (Chrompack). Bupropion base was detected by UV absorption at 310 nm using a Spectra 100 spectrophotometer (Spectra-Physics, Breda, The Netherlands). Chromatograms were integrated by WOW integrated computer program.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A transdermal method of treating a mammalian; subject with a bupropion composition, consisting essentially of the steps of:

stabilizing a bupropion base selected from the group which consists of (+)-bupropion base, (−)-bupropion base and racemic bupropion base and mixtures thereof by combining the bupropion base with at least one stabilizer capable of stabilizing the bupropion base in the absence of any additional base and forming a composition capable of transferring across a semipermeable human dermal layer;

incorporating the stabilized bupropion base on a support in a transdermal patch having a bupropion-transfer surface area adapted to contact the skin of the patient and sufficient to transfer a therapeutically effective amount of bupropion base through the skin of said patient into the bloodstream of said patient, said patch containing bupropion base as the sole base; and adhering said patch to the skin of the patient for a period of days to deliver a bupropion dosage of substantially 10 mg/day to 300 mg/day to said patient.

2. The transdermal method of treatment defined in claim 1 wherein the stabilizer is a pharmaceutically acceptable organic acid ester.

3. The transdermal method of treatment defined in claim 1 wherein the stabilizer is selected from the group consisting of 1-ascorbic acid palmitate, tocopherol solution in alcohol, butylated hydroxy anisole, Vitamin E succinate, Vitamin E 700 acetate, and L-ascorbic acid G palmitate and is present in the bupropion composition in an amount of 2.7 to 27% by weight of the bupropion base.

4. A patch for transdermal delivery of bupropion to a mammalian subject, said patch comprising:

(a) a flexible, inert backing layer incapable of absorbing bupropion base;

(b) a release liner through which bupropion base is not permeable; and (c) a reservoir located between the backing layer and the release liner, said reservoir having a bupropion-transfer surface adjacent to the release liner and adapted to contact the skin of the patient and sufficient to transfer an effective dosage of bupropion base through the skin of said patient into the bloodstream of said patient, said reservoir containing bupropion base as the sole base, which consisting essentially of comprises:

(i) a therapeutically effective amount of bupropion base selected from the group which consists of (+)-bupropion base, (−)-bupropion base and racemic bupropion base and mixtures thereof on said support;

(ii) at least one stabilizer capable of stabilizing the bupropion base in said reservoir, said stabilizer selected from the group consisting of Vitamin E and butylated hydroxy anisole; and (iii) means for securing the bupropion-transfer surface area of said reservoir to the skin of the patient.

5. The patch for transdermal delivery of bupropion defined in claim 4 wherein the stabilizer is present in the bupropion composition in an amount of 2.7 to 27% by weight of the bupropion base.

6. The patch for transdermal delivery of bupropion defined in claim 5 wherein the stabilizer is present in an amount of 3 to 15% by weight of the bupropion base.

7. The patch for transdermal delivery of bupropion defined in claim 6 wherein the stabilizer is present in an amount of 5 to 8% by weight of the bupropion base.

8. The patch for transdermal delivery of bupropion defined in claim 4 wherein the Vitamin E is included as tocopherol solution in alcohol, Vitamin E succinate, and Vitamin E 700 acetate.

9. The patch for transdermal delivery of bupropion defined in claim 4 wherein the reservoir further comprises a carrier or vehicle selected from the group consisting of water, silicone, liquid sugars, waxes and petroleum jelly.

10. The patch for transdermal delivery of bupropion defined in claim 4 wherein the reservoir further comprises a dispersing agent.

11. The patch for transdermal delivery of bupropion defined in claim 4 wherein the reservoir further comprises a non-ionic excipient.

12. The patch for transdermal delivery of bupropion defined in claim 4 wherein the means for securing the bupropion-transfer surface area Of said reservoir to the skin of the patient is a pressure-sensitive adhesive selected from the group consisting of polyisobutylenes, silicones, polyurethanes, and polyacrylates.

13. The patch for transdermal delivery of bupropion defined in claim 4 wherein the backing layer is selected from the group consisting of polyesters, polyethylene, polypropylene, polyurethanes, and polyether amides.

14. The patch for transdermal delivery of bupropion defined in claim 4 wherein the release liner is a silicone-coated polyester.

* * * * *